(12) United States Patent
Deng

(10) Patent No.: US 10,123,431 B2
(45) Date of Patent: Nov. 6, 2018

(54) METHODS OF DEFECT INSPECTION OF PLATED THROUGH HOLE STRUCTURES UTILIZING FLUORESCENT CONDUCTIVE FILL MATERIAL

(71) Applicant: Intel Corporation, Santa Clara, CA (US)

(72) Inventor: Yikang Deng, Chandler, AZ (US)

(73) Assignee: Intel Corporation, Santa Clara, CA (US)

(*) Notice: Subject to any disclaimer, the term of this patent is extended or adjusted under 35 U.S.C. 154(b) by 189 days.

(21) Appl. No.: 15/170,444

(22) Filed: Jun. 1, 2016

(65) Prior Publication Data

US 2016/0278218 A1    Sep. 22, 2016

Related U.S. Application Data

(62) Division of application No. 14/244,142, filed on Apr. 3, 2014, now abandoned.

(51) Int. Cl.
*H05K 3/42* (2006.01)
*G01N 21/95* (2006.01)
(Continued)

(52) U.S. Cl.
CPC ............... *H05K 3/42* (2013.01); *G01N 21/64* (2013.01); *G01N 21/643* (2013.01); *G01N 21/95* (2013.01); *H05K 1/0269* (2013.01); *H05K 1/0274* (2013.01); *H05K 1/0298* (2013.01); *H05K 3/0011* (2013.01); *G01N 21/6456* (2013.01); *G01N 2021/646* (2013.01); *G01N 2021/6439* (2013.01); *H05K 1/09* (2013.01); *H05K 1/115* (2013.01); *H05K 3/426* (2013.01);
(Continued)

(58) Field of Classification Search
CPC ...... H05K 3/4661; H05K 3/42; H05K 3/0032; H05K 3/426; H05K 2201/0959; H05K 2201/09827; H05K 2201/09845
See application file for complete search history.

(56) References Cited

U.S. PATENT DOCUMENTS

| | | | | |
|---|---|---|---|---|
| 5,122,737 A | * | 6/1992 | Clauberg | G01R 31/308 324/73.1 |
| 5,301,012 A | * | 4/1994 | King | G01N 21/95692 356/237.1 |

(Continued)

*Primary Examiner* — Minh Trinh
(74) *Attorney, Agent, or Firm* — Green, Howard & Mughal LLP.

(57) ABSTRACT

A microelectronic substrate may be fabricated having a substrate core with at least one plated through hole extending therethrough, wherein the plated through hole includes a fluorescent conductive fill material which can be utilized to detect defects during the fabrication process. In one embodiment, the microelectronic substrate may be fabricated by forming a substrate core, forming a hole to extend from a first surface to an opposing second surface of the substrate core, forming a conductive material layer on a sidewall(s) of the substrate core hole, disposing a fluorescent conductive fill material to abut the conductive material layer and fill the remaining substrate core hole, illuminating an exposed portion of the fluorescent conductive fill material, and detecting anomalies in the light fluoresced by the exposed portion of the fluorescent conductive fill material.

15 Claims, 7 Drawing Sheets

(51) Int. Cl.
*G01N 21/64* (2006.01)
*H05K 1/02* (2006.01)
*H05K 3/00* (2006.01)
H05K 1/11 (2006.01)
H05K 1/09 (2006.01)
H05K 3/46 (2006.01)

(52) U.S. Cl.
CPC ... *H05K 3/4644* (2013.01); *H05K 2201/0302* (2013.01); *H05K 2201/0326* (2013.01); *H05K 2201/0329* (2013.01); *H05K 2203/163* (2013.01); *Y10T 29/49165* (2015.01)

(56) References Cited

U.S. PATENT DOCUMENTS

| | | | |
|---|---|---|---|
| 5,891,606 A * | 4/1999 | Brown | H05K 1/115 216/18 |
| 6,114,098 A * | 9/2000 | Appelt | H05K 3/4053 427/97.2 |
| 6,197,664 B1 * | 3/2001 | Lee | H05K 3/423 216/17 |
| 6,376,049 B1 | 4/2002 | Asai et al. | |
| 8,156,645 B2 * | 4/2012 | Sidhu | H05K 1/116 174/262 |
| 2005/0126818 A1 | 6/2005 | Kojima et al. | |
| 2007/0105248 A1 * | 5/2007 | Katoh | G01R 31/2891 438/17 |
| 2009/0041669 A1 | 2/2009 | Renard et al. | |
| 2009/0294691 A1 | 12/2009 | Trinquet et al. | |
| 2010/0006324 A1 | 1/2010 | Kitamura et al. | |
| 2011/0247860 A1 * | 10/2011 | Yoshioka | H05K 3/107 174/250 |
| 2013/0233607 A1 * | 9/2013 | Nakamura | H05K 1/0206 174/262 |
| 2015/0089806 A1 * | 4/2015 | Roy | H01L 23/49822 29/852 |
| 2015/0289372 A1 * | 10/2015 | Deng | H05K 3/42 361/679.02 |

* cited by examiner

METHODS OF DEFECT INSPECTION OF PLATED THROUGH HOLE STRUCTURES UTILIZING FLUORESCENT CONDUCTIVE FILL MATERIAL

RELATED APPLICATION

The present application is a divisional of U.S. patent application Ser. No. 14/244,142, filed on Apr. 3, 2014, entitled "FLUORESCENT CONDUCTIVE FILL MATERIAL FOR PLATED THROUGH HOLE STRUCTURES AND METHODS OF DEFECT INSPECTION UTILIZING THE SAME" which is hereby incorporated herein by reference in its entirety and for all purposes.

TECHNICAL FIELD

Embodiments of the present description generally relate to the field of microelectronic packaging, and, more particularly, to a microelectronic substrate including a substrate core having at least one plated through hole extending therethrough, wherein the plated through hole includes a fluorescent conductive fill material, and to methods of utilizing the fluorescent conductive fill material for the detection of defects.

BACKGROUND

The microelectronic industry is continually striving to produce ever faster and smaller microelectronic packages for use in various electronic products, including, but not limited to, computer server products and portable products, such as portable computers, electronic tablets, cellular phones, digital cameras, and the like. As these goals are achieved, microelectronic dice become smaller, and, with higher performance, comes an ever increasing number of interconnects on the active surface of a microelectronic die with an ever decreasing pitch.

Microelectronic dice are typically mounted on microelectronic substrates for packaging purposes, wherein the microelectronic substrates typical comprise a substrate core (e.g., bismaleimide triazine resin, FR4, polyimide materials, and the like) having dielectric layers (e.g., epoxy resin, polyimide, bisbenzocyclobutene, and the like) and conductive traces (e.g., copper, aluminum, and the like) formed on a first surface thereof to form a top trace network, and having dielectric layers and conductive traces formed on an opposing second surface thereof to form a bottom trace network. To achieve electrical interconnection between the top trace network and the bottom trace network, prior to forming the top and bottom trace networks, holes are drilled through the substrate core in specific locations. These holes are plated with a conductive material layer and filled with a conductive fill material to form what is known in the art as "plated through holes". However, as these plated through holes become smaller, it becomes more difficult to fill them with the conductive fill material. For example, air pockets or bubbles may become trapped in the holes during the filling process, known as a "plug dent" defect. Such air pockets may result in a plated through hole which does not have sufficient current carrying capacity, which may result in the failure of the microelectronic package.

BRIEF DESCRIPTION OF THE DRAWINGS

The subject matter of the present disclosure is particularly pointed out and distinctly claimed in the concluding portion of the specification. The foregoing and other features of the present disclosure will become more fully apparent from the following description and appended claims, taken in conjunction with the accompanying drawings. It is understood that the accompanying drawings depict only several embodiments in accordance with the present disclosure and are, therefore, not to be considered limiting of its scope. The disclosure will be described with additional specificity and detail through use of the accompanying drawings, such that the advantages of the present disclosure can be more readily ascertained, in which:

DESCRIPTION OF EMBODIMENTS

Figure 1:
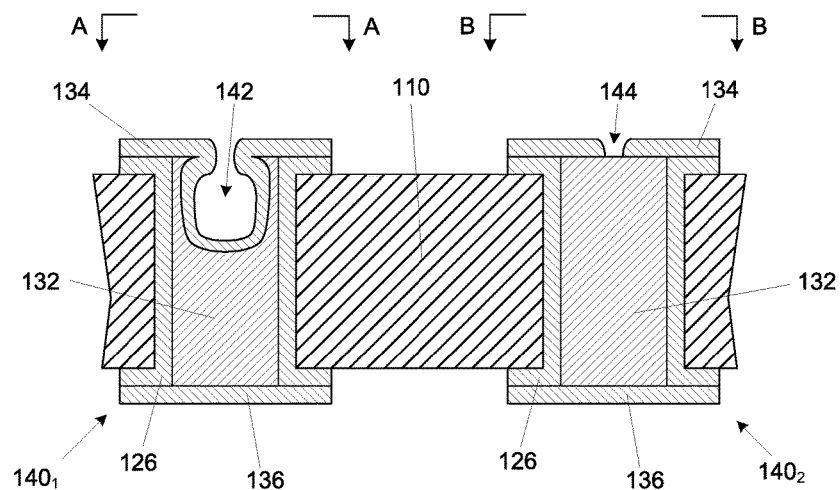
FIG. 1 illustrates a cross-sectional view of plated through holes having defects, as known in the art.

In the following detailed description, reference is made to the accompanying drawings that show, by way of illustration, specific embodiments in which the claimed subject matter may be practiced. These embodiments are described in sufficient detail to enable those skilled in the art to practice the subject matter. It is to be understood that the various embodiments, although different, are not necessarily mutually exclusive. For example, a particular feature, structure, or characteristic described herein, in connection with one embodiment, may be implemented within other embodiments without departing from the spirit and scope of the claimed subject matter. References within this specification to "one embodiment" or "an embodiment" mean that a particular feature, structure, or characteristic described in connection with the embodiment is included in at least one implementation encompassed within the present description. Therefore, the use of the phrase "one embodiment" or "in an embodiment" does not necessarily refer to the same embodiment. In addition, it is to be understood that the location or arrangement of individual elements within each disclosed embodiment may be modified without departing from the spirit and scope of the claimed subject matter. The following detailed description is, therefore, not to be taken in a limiting sense, and the scope of the subject matter is defined only by the appended claims, appropriately interpreted, along with the full range of equivalents to which the appended claims are entitled. In the drawings, like numerals refer to the same or similar elements or functionality throughout the several views, and that elements depicted therein are not necessarily to scale with one another, rather individual elements may be enlarged or reduced in order to more easily comprehend the elements in the context of the present description.

The terms "over", "to", "between" and "on" as used herein may refer to a relative position of one layer with respect to other layers. One layer "over" or "on" another layer or bonded "to" another layer may be directly in contact with the other layer or may have one or more intervening layers. One layer "between" layers may be directly in contact with the layers or may have one or more intervening layers.

Embodiments of the present description include a microelectronic substrate having a substrate core with at least one plated through hole extending therethrough, wherein the plated through hole includes a fluorescent conductive fill material. In one embodiment, the plated through hole may comprise a hole defined to extend from a first surface to an opposing second surface of the substrate core, wherein a conductive material layer is formed on a sidewall(s) of the substrate core hole and a conductive fill material, having a fluorescent component, is disposed to fill the remaining substrate core hole after forming the conductive material layer. In another embodiment, the fluorescent conductive fill material is used for the detection of defects.

Figure 2:
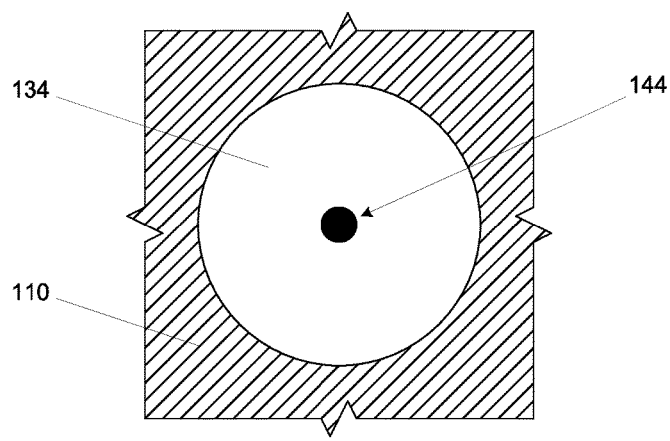
FIG. 2 illustrates a top plan view along either line A-A or B-B of FIG. 1, as known in the art.

FIG. 1 illustrates a pair of plated through holes (illustrated as elements $140_1$ and $140_2$) having defects. Plated through hole $140_1$ illustrates a defect known as a "plug dent". A plug dent defect generally occurs during the deposition of the conductive fill material 132 used to form the plated through hole $140_1$, wherein air bubbles 142 become trapped in the conductive fill material 132. Such air bubbles 142 may reduce the current carrying capacity of the plated through hole $140_1$. Plated through hole $140_2$ illustrates a defect known as a "copper missing" defect. A copper missing defect generally occurs during an electroless plating process used to form capping layers 134, 136 for the plated through holes $140_1$, $140_2$, wherein complete coverage is not achieved. In general, the defect shown in plated through hole $140_1$ is a fatal defect, requiring scrapping or reworking, and the defect shown in plated through hole $140_2$ is not. However, it may be difficult to differentiate between a plug dent defect and a copper missing defect (or similar defects), because when a defect inspection is conducted, such as with an automated optical inspection device inspecting along line A-A for plated through hole $140_1$ and along line B-B for plated through hole $140_2$, both defects show up as an anomaly or "black dot" 144, as illustrated in FIG. 2. Thus, more extensive cross-section analysis may be required to determine the actual type of the defect. However, even though cross-section images may be available on units rejected by an automated optical inspection, the associated manufacturing lot may have already passed the fabrication process and, thus, the opportunity of immediate engineering response may have been missed.

Figure 3:
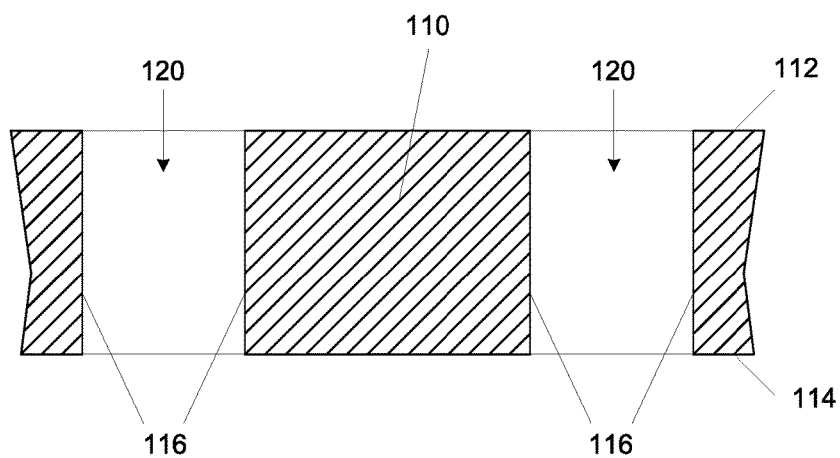
FIGS. 3-9 illustrates cross-sectional and plan views of processes of fabricating and inspecting a microelectronic substrate, according to an embodiment of the present description.

FIGS. 3-9 illustrate embodiments of the present description wherein a microelectronic substrate is formed with plated through holes having a fluorescent conductive fill material. The processes used in forming microelectronic substrates are well known to those skilled in the art, and for the sake of brevity and conciseness will not be described with specificity. As illustrated in FIG. 3, a substrate core 110 may be fabricated having holes 120 formed to extend from a first surface 112 of the substrate core 110 to a second surface 114 of the substrate core 110 defining at least one sidewall 116 therebetween. The substrate core 110 may be made of any appropriate substantially rigid material, including, but not limited to, bismaleimide triazine resin, FR4, polyimide materials, and the like. The substrate core holes 120 may be made by any appropriate technique in the art, including, but not limited to, laser drilling, photolithography, and ion bombardment.

Figure 4:
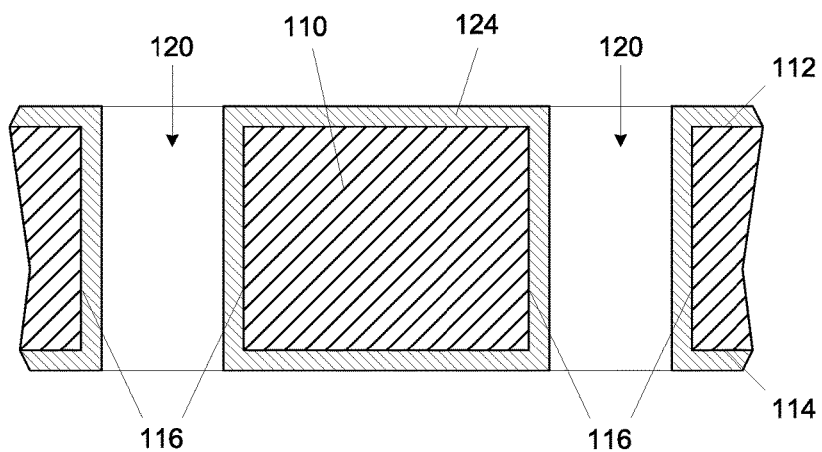

As shown in FIG. 4, a conductive material layer 124 may be plated or otherwise deposited over the substrate core first surface 112, the substrate core second surface 114, and the substrate core hole sidewalls 116. As illustrated, in one embodiment, the conductive material layer 124 may form a substantially uniform coating over the substrate core first surface 112, the substrate core second surface 114, and the substrate core hole sidewalls 116. The conductive material layer 124 may be any appropriate material, such as a metal, including copper, silver, gold, nickel, titanium, tungsten, and alloys thereof.

Figure 5:
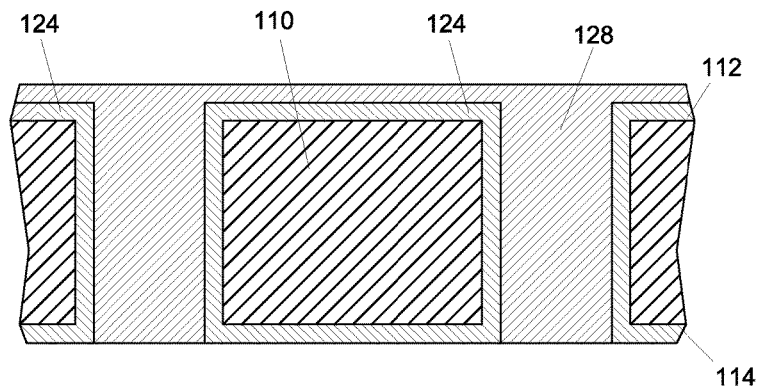

As shown in FIG. 5, a fluorescent conductive fill material 128 (e.g., a conductive fill material having a fluorescing component therein) may be deposited in the substrate core holes 120 (see FIG. 4). For example, the substrate core 110 may be placed with its second surface 114 adjacent a carrier (not shown) and the conductive fill material 128 may be deposited from the first surface 112 side of the substrate core 110. Such that a portion of the fluorescent conductive fill material 128 may extend over the conductive material layer 124 adjacent the substrate core first surface 112. The fluorescent conductive fill material 128 may be deposited by any known technique in the art, including, but not limited to, printing, spin coating, chemical vapor, deposition, physical vapor, deposition, and the like.

In one embodiment, the fluorescent conductive fill material 128 may comprise epoxy resin, silicon dioxide, epoxy hardener, and the like, having a fluorescent component dispersed therein. The fluorescent component may include, but is not limited to rhodamine, fluorescein, cyanine, and inorganic quantum dots. The fluorescent component may comprise between about 0.5% and 50% by weight of the fluorescent conductive fill material 128.

Figure 6:
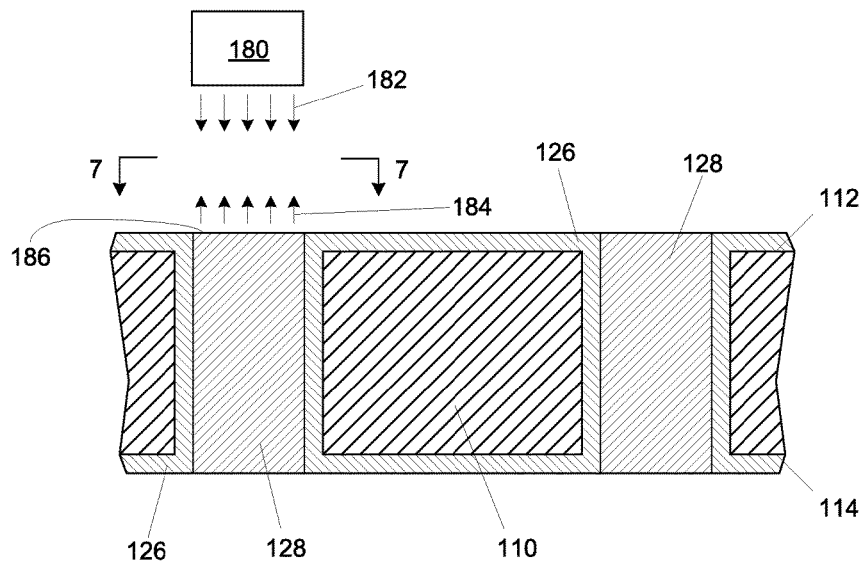

As shown in FIG. 6, the portion of the fluorescent conductive fill material 128 that may extend over the conductive material layer 124 adjacent the substrate core first surface 112 may be removed by any technique known in the art, such as grinding, etching, chemical mechanical polishing, and the like. This may result in the fluorescent conductive fill material 128 only filling the substrate core holes 120 (see FIG. 4) remaining after forming the conductive material layer 124.

Figure 7:
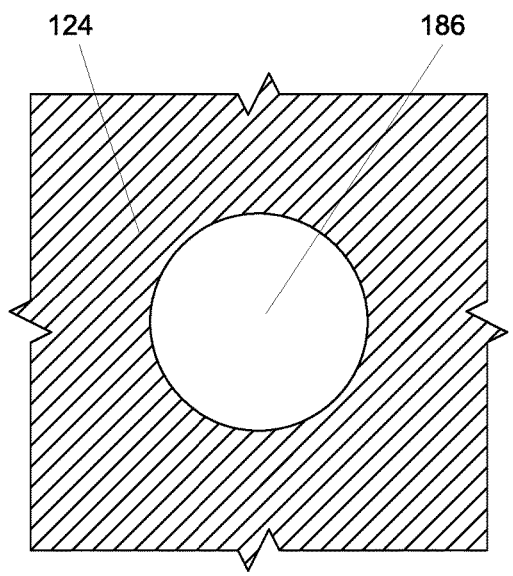

As will be understood to those skilled in the art, a fluorescent material is a substance the absorbs electromagnetic radiation (such a light), usually short-wavelength light (such as ultraviolet light), and re-emits it almost instantaneously at a different wavelength (usually longer) than the absorbed electromagnetic radiation. As further shown in FIG. 6, an automated optical inspection system 180 may be used to transmit electromagnetic radiation (shown as arrows 182) toward an exposed surface 186 of the fluorescent conductive fill material 128, which re-emits or fluoresces electromagnetic radiation (shown as arrows 184) at a wavelength different than the transmitted electromagnetic radiation 182 from the optical inspection system 180. The optical inspection system 180 may detect the fluoresced electromagnetic radiation 184. As shown in FIG. 7 (view along line 7-7 of FIG. 6), if no defects exist in the fluorescent conductive fill material exposed surface 186, a substantially uniform fluoresced electromagnetic radiation 184 pattern will be detected across the fluorescent conductive fill material exposed surface 186 (shown generally as the uniform blank or white fluorescent conductive fill material exposed surface 186 in FIG. 7). If a defect exists in the fluorescent conductive fill material exposed surface 186, a wavelength anomaly in fluoresced electromagnetic radiation 184 will be detected, such as the "black dot 144" of FIG. 2.

Figure 8:
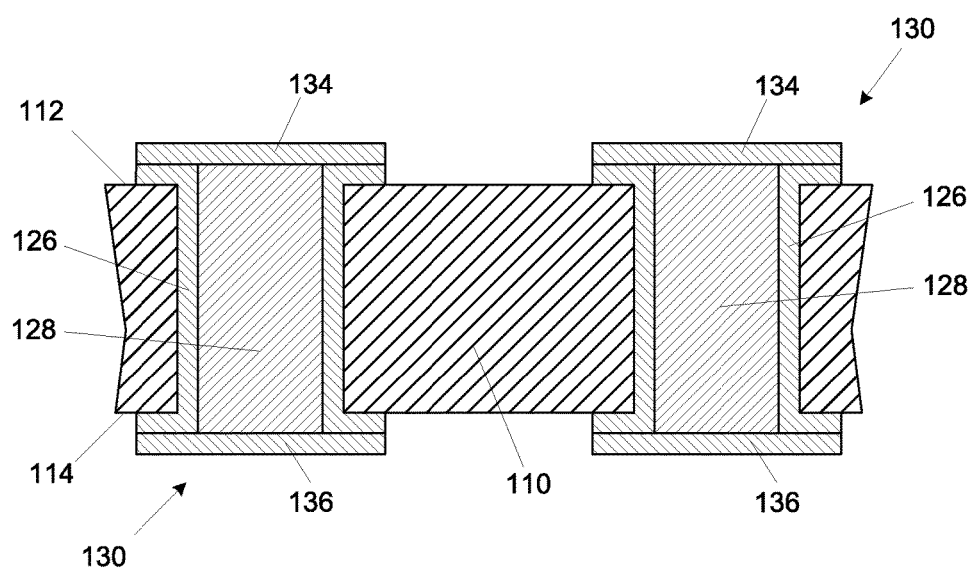

As shown in FIG. 8, after the fluorescent conductive fill material 128 has passed inspection, capping conductive material layers (not shown) may be formed on the fluorescent conductive fill material 128 and the conductive material layer 124 proximate the substrate core first surface 112 and on the fluorescent conductive fill material 128 and the conductive material layer 124 proximate the substrate core second surface 114. Portion of the capping conductive material layers (not shown) and the conductive material layer 124 may be proximate on the substrate core first surface 112 and the substrate core second surface 114 to separate the conductive material layer 124 into individual conductive material liners 126 within each of substrate core holes 120 (see FIG. 4) and form first capping layers 134 may be formed on the fluorescent conductive fill material 128 proximate the substrate core first surface 112 and second capping layers 136 may be formed on the fluorescent conductive fill material 128 proximate the substrate core second surface 114 to form plated through holes 130. The portions of the conductive material layer 124 may be removed by any known technique known in the art, including, but not limited to, photolithographic techniques.

Figure 9:
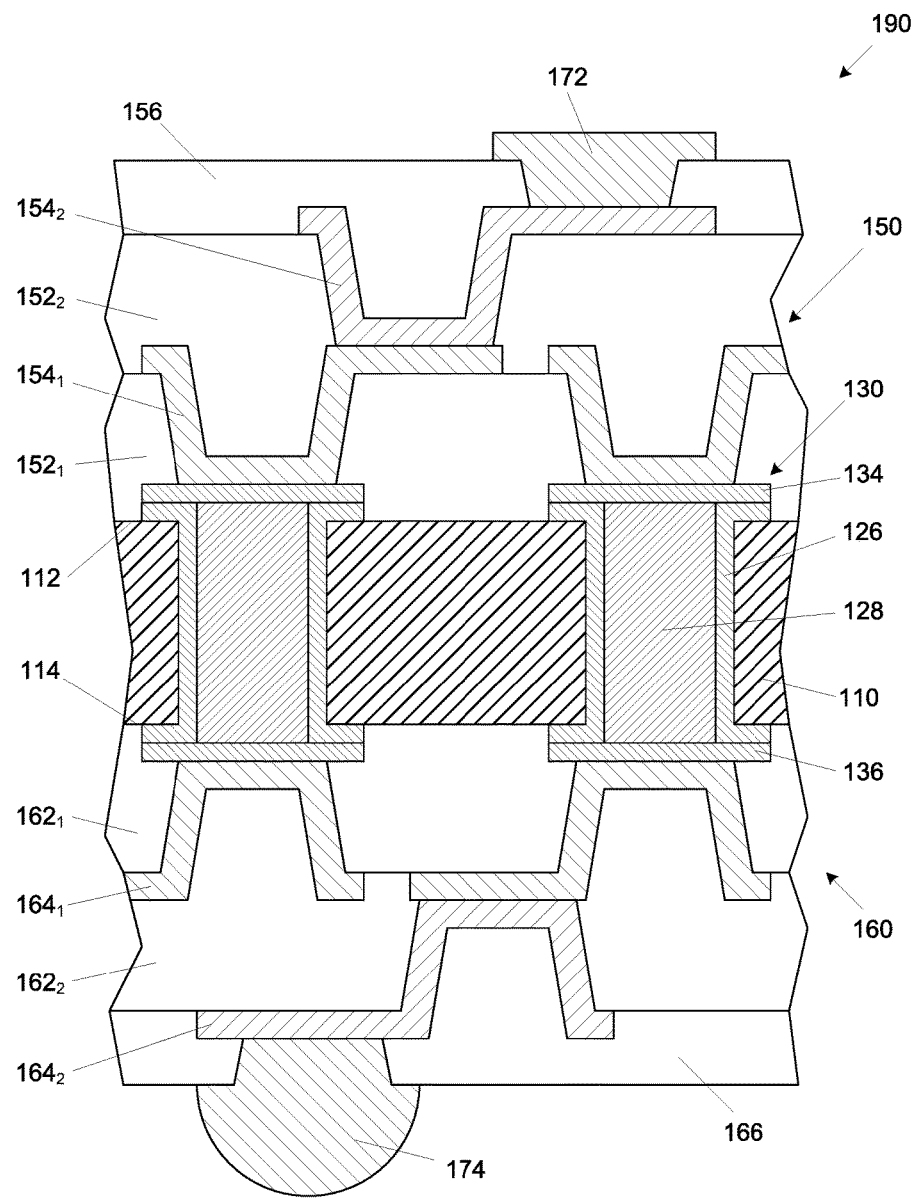

As shown in FIG. 9, a microelectronic substrate 190 may be formed using the substrate core 110 and plated through holes 130 shown in FIG. 8. A top trace network 150 may be formed proximate the substrate core first surface 112 comprising dielectric layers (shown as elements $152_1$ and $152_2$) and conductive traces (shown as elements $154_1$ and $154_2$), which are formed on and extend through their respective dielectric layer $152_1$, $152_2$. A bottom trace network 160 may be formed proximate the substrate core second surface 114 comprising dielectric layers (shown as elements $162_1$ and $162_2$) and conductive traces (shown as elements $164_1$ and $164_2$), which are formed on and extend through their respective dielectric layer $162_1$, $162_2$. A first outer dielectric layer 156, such as a solder resist layer, may be formed on the top trace network 150 and a connection structure (shown as a bond pad 172) may be formed therein. A second outer dielectric layer 166, such as a solder resist layer, may be form on the bottom trace network 160 and a connection structure (shown as a solder bump 174) may be formed therein.

The dielectric layers $152_1$, $152_2$, $162_1$, and $162_2$ may comprise any appropriate dielectric material, including, by not limited to, liquid crystal polymer, epoxy resin, bismaleimide triazine resin, polybenzoxazole, polyimide material, silica-filled epoxy (such as materials available from Ajinomoto Fine-Techno Co., Inc., 1-2 Suzuki-cho, Kawasaki-ku, Kawasaki-shi, 210-0801, Japan (e.g. Ajinomoto ABF-GX13, and Ajinomoto GX92)), and the like. The conductive traces $154_1$, $154_2$, $164_1$, and $164_2$ may be formed of any appropriate conductive material, including, but not limited to, copper, silver, gold, nickel, titanium, tungsten, and alloys thereof. The processes used for forming the top and bottom trace networks 150, 160 are well known to those skilled in the art, and for the sake of brevity and conciseness will not be described or illustrated herein. It is understood that the top and bottom trace networks 150, 160 may be formed from any number of dielectric layers and conductive traces.

Embodiments of the present description may have advantages over existing processes. As will be understood to those skilled in the art, embodiments of the present description may provide an inline inspection metrology which can quickly and accurately detect the defects in the conductive fill material without waiting for cross-section analysis after the completion of substrate core formation process. This may provide higher throughput (no need of time-consuming cross-section analysis), faster data turnaround (no need to wait for substrate core formation), higher inspection accuracy (no "soft error" due to other plating related defects). Furthermore, there is no need to change the process of depositing the conductive fill material or change the overall substrate core formation process.

Figure 10:
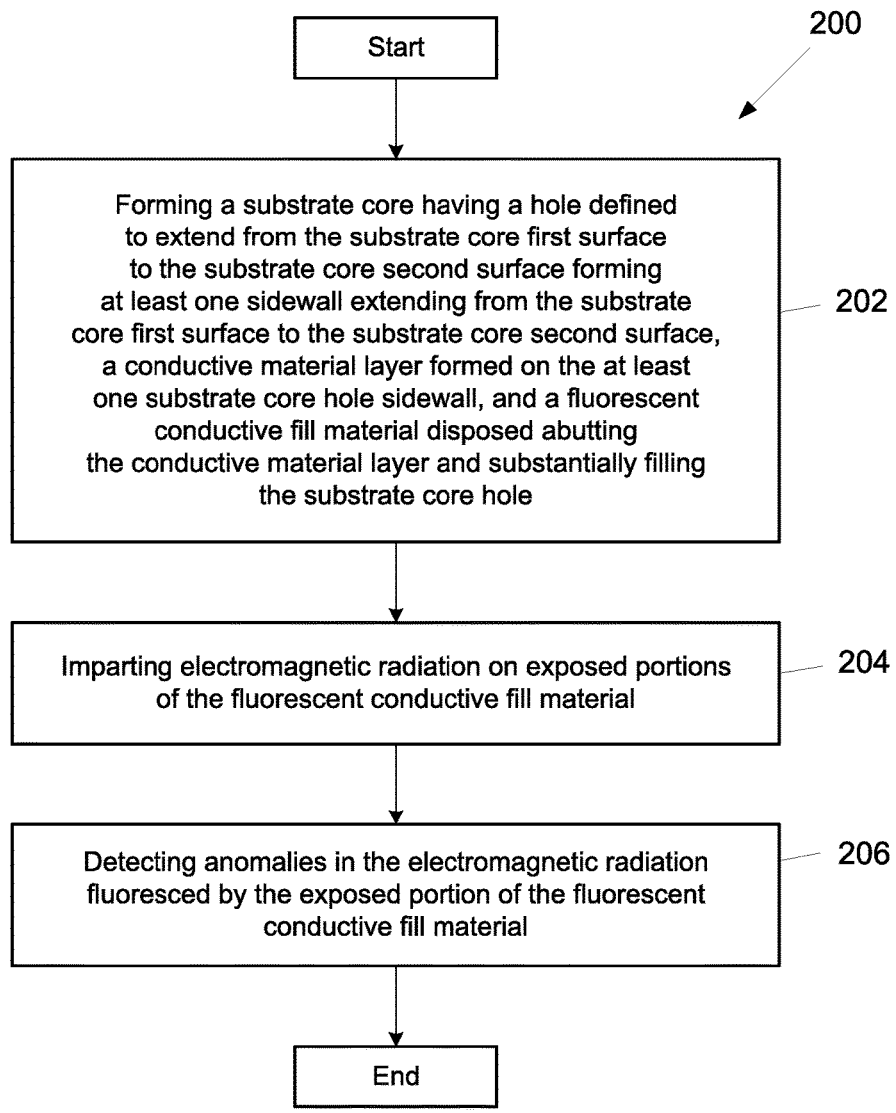
FIG. 10 is a flow chart of a process of inspecting a microelectronic structure, according to an embodiment of the present description.

FIG. 10 is a flow chart of a process 200 of detecting a defect in a plated through hole according to an embodiment of the present description. As set forth in block 202, a substrate core may be formed having a hole defined to extend from the substrate core first surface to the substrate core second surface forming at least one sidewall, a conductive material layer formed on the at least one substrate core hole sidewall, and a fluorescent conductive fill material disposed abutting the conductive material layer and substantially filling the substrate core hole. Electromagnetic radiation may be imparted on exposed portions of the fluorescent conductive fill material, as set forth in block 204. As set forth in block 206, anomalies in the electromagnetic radiation fluoresced by the exposed portion of the fluorescent conductive fill material may be detected.

Figure 11:
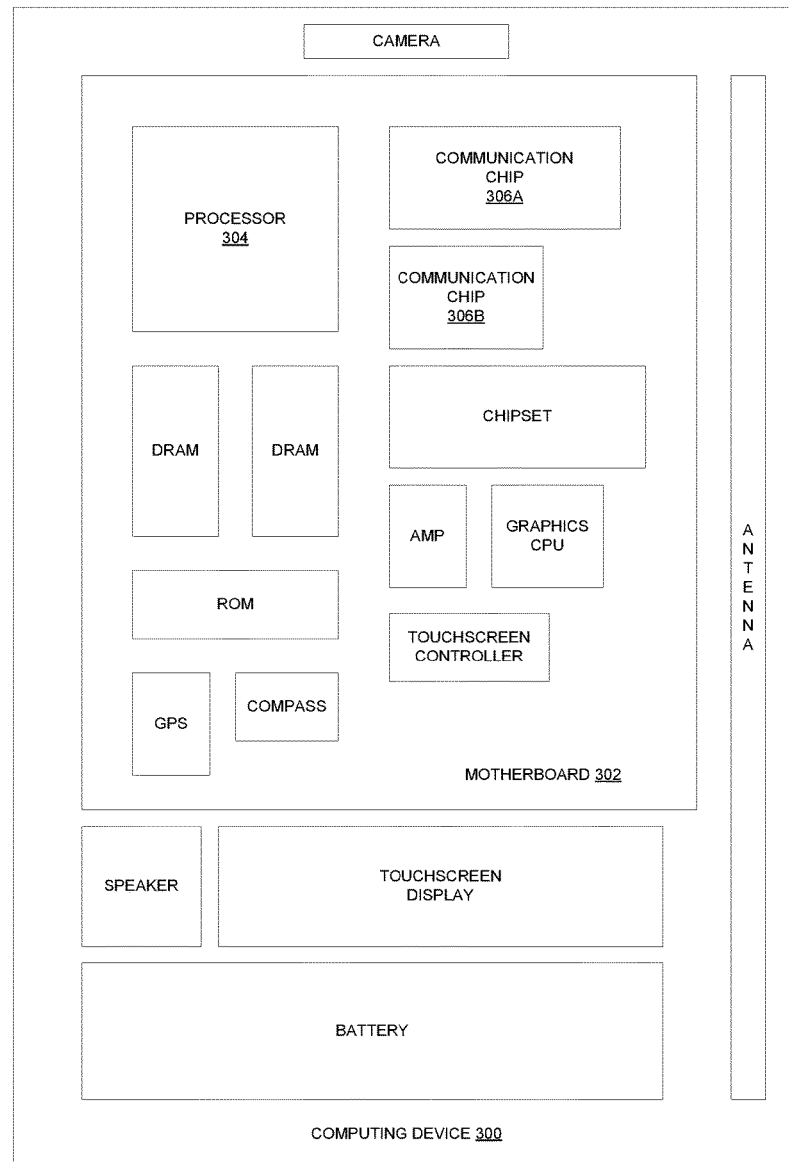
FIG. 11 illustrates a computing device in accordance with one implementation of the present description.

FIG. 11 illustrates a computing device 300 in accordance with one implementation of the present description. The computing device 300 houses a board 302. The board 302 may include a number of components, including but not limited to a processor 304 and at least one communication chip 306A, 306B. The processor 304 is physically and electrically coupled to the board 302. In some implementations the at least one communication chip 306A, 306B is also physically and electrically coupled to the board 302. In further implementations, the communication chip 306A, 306B is part of the processor 304.

Depending on its applications, the computing device 300 may include other components that may or may not be physically and electrically coupled to the board 302. These other components include, but are not limited to, volatile memory (e.g., DRAM), non-volatile memory (e.g., ROM), flash memory, a graphics processor, a digital signal processor, a crypto processor, a chipset, an antenna, a display, a touchscreen display, a touchscreen controller, a battery, an audio codec, a video codec, a power amplifier, a global positioning system (GPS) device, a compass, an accelerometer, a gyroscope, a speaker, a camera, and a mass storage device (such as hard disk drive, compact disk (CD), digital versatile disk (DVD), and so forth).

The communication chip 306A, 306B enables wireless communications for the transfer of data to and from the computing device 300. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 306 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. The computing device 300 may include a plurality of communication chips 306A, 306B. For instance, a first communication chip 306A may be dedicated to shorter range wireless communications such as Wi-Fi and Bluetooth and a second communication chip 306B may be dedicated to longer range wireless communications such as GPS, EDGE, GPRS, CDMA, WiMAX, LTE, Ev-DO, and others.

The processor 304 of the computing device 300 may include a microelectronic package having a microelectronic substrate having a fluorescent conductive fill material within a plated through hole, as described above. The term "processor" may refer to any device or portion of a device that processes electronic data from registers and/or memory to transform that electronic data into other electronic data that may be stored in registers and/or memory.

The communication chip 306A, 306B may include a microelectronic package having a microelectronic substrate having a fluorescent conductive fill material within a plated through hole, as described above.

In various implementations, the computing device 300 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In further implementations, the computing device 300 may be any other electronic device that processes data.

It is understood that the subject matter of the present description is not necessarily limited to specific applications illustrated in FIGS. 3-11. The subject matter may be applied to other microelectronic devices and assembly applications, as well as any appropriate electronic application, as will be understood to those skilled in the art.

The following examples pertain to further embodiments. Specifics in the examples may be used anywhere in one or more embodiments.

In Example 1, a microelectronic substrate may comprise a substrate core having at least one plated through hole extending from a first surface of the substrate core to a second surface of the substrate core, wherein the plated through hole comprises a hole defined to extend from the substrate core first surface to the substrate core second surface forming at least one sidewall, a conductive material liner formed on the at least one substrate core hole sidewall, and a fluorescent conductive fill material disposed to abut the conductive material liner and substantially fill the substrate core hole.

In Example 2, the subject matter of Example 1 can optionally include the fluorescent conductive fill material comprising an epoxy resin having a fluorescent component dispersed therein.

In Example 3, the subject matter of Example 1 or 2 can optionally include the fluorescent conductive fill material including a fluorescent component selected from the group consisting of rhodamine, fluorescein, cyanine, and inorganic quantum dots.

In Example 4, the subject matter of any of Examples 1 to 3 can optionally include the fluorescent conductive fill material including a fluorescent component comprising between about 0.5% and 50% by weight of the fluorescent conductive fill material.

In Example 5, a method of fabricating a microelectronic substrate may comprise forming a substrate core having a first surface and an opposing second surface, forming a hole to extend from the substrate core first surface to the substrate core second surface defining at least one sidewall, forming a conductive material layer on the at least one substrate core hole sidewall, and disposing a fluorescent conductive fill material to abut the conductive material layer and substantially fill the substrate core hole.

In Example 6, the subject matter of Example 5 can optionally include disposing the fluorescent conductive fill material comprising disposing a fluorescent conductive fill material comprising an epoxy resin having a fluorescent component dispersed therein.

In Example 7, the subject matter of any of Examples 5 to 6 can optionally include disposing the fluorescent conductive fill material comprising disposing a fluorescent conductive fill material including a fluorescent component selected from the group consisting of rhodamine, fluorescein, cyanine, and inorganic quantum dots.

In Example 8, the subject matter of any of Examples 5 to 7 can optionally include disposing the fluorescent conductive fill material including disposing a fluorescent conductive fill material having a fluorescent component comprising between about 0.5% and 50% by weight of the fluorescent conductive fill material.

In Example 9, the subject matter of any of Examples 5 to 8 can optionally include forming a conductive material layer on the at least one substrate core hole sidewall comprising depositing a conductive material layer on the substrate core first surface, the substrate core second surface, and the at least one substrate core hole sidewall.

In Example 10, the subject matter of any of Examples 5 to 9 can optionally include depositing the conductive material layer comprising depositing a substantially uniform layer of conductive material on the substrate core first surface, the substrate core second surface, and the at least one substrate core hole sidewall.

In Example 11, the subject matter of any of Examples 5 to 10 can optionally include depositing the conductive material layer comprising plating a metal material.

In Example 12, the subject matter of any of Examples 5 to 11 can optionally include disposing the fluorescent conductive fill material into the substrate core hole and over the conductive material layer proximate the substrate core first surface; and further including removing a portion of the fluorescent conductive fill material over the conductive material layer proximate the substrate core first surface.

In Example 13, the subject matter of any of Examples 5 to 12 can optionally include forming a first capping conductive material layer on the fluorescent conductive fill material and the conductive material layer proximate the substrate core first surface, forming a second capping conductive material layer on the fluorescent conductive fill material and the conductive material layer proximate the substrate core second surface, removing a portion of the first capping conductive material layer and the conductive material layer proximate the substrate core first surface, and removing a portion of the second capping conductive material layer and the conductive material layer proximate to substrate core second surface to separate the conductive material layer into individual conductive material liners within each of substrate core holes and form first capping layers on the fluorescent conductive fill material proximate the substrate core first surface and second capping layers on the fluorescent conductive fill material proximate the substrate core second surface.

In Example 14, a method of detecting a defect in a plated through hole may comprise forming a substrate core having a hole defined to extend from the substrate core first surface to the substrate core second surface forming at least one sidewall, a conductive material layer formed on the at least one substrate core hole sidewall; and a fluorescent conductive fill material disposed abutting the conductive material layer and substantially filling the substrate core hole, illuminating an exposed portion of the fluorescent conductive fill material, and detecting anomalies in the light fluoresced by the exposed portion of the fluorescent conductive fill material.

In Example 15, the subject matter of Example 14 can optionally include forming the substrate core comprising forming the substrate core having the fluorescent conductive fill material comprising an epoxy resin having a fluorescent component dispersed therein.

In Example 16, the subject matter of any of Examples 14 to 15 can optionally include forming the substrate core comprises forming the substrate core having the fluorescent conductive fill material comprising a fluorescent component selected from the group consisting of rhodamine, fluorescein, cyanine, and inorganic quantum dots.

In Example 17, the subject matter of any of Examples 14 to 17 can optionally include forming the substrate core comprises forming the substrate core having the fluorescent conductive fill material comprising a fluorescent component comprising between about 0.5% and 50% by weight of the fluorescent conductive fill material.

In Example 18, a computing device, comprising a board, and a microelectronic package attached to the board, wherein the microelectronic package comprising a microelectronic substrate, comprising a substrate core having at least one plated through hole extending from a first surface of the substrate core to a second surface of the substrate core, wherein the plated through hole comprises a hole defined to extend from the substrate core first surface to the substrate core second surface forming at least one sidewall, a conductive material liner is formed on the at least one substrate core hole sidewall, and a fluorescent conductive fill material disposed to abut the conductive material liner and substantially fill the substrate core hole.

In Example 19, the subject matter of Example 18 can optionally include the fluorescent conductive fill material including a fluorescent component selected from the group consisting of rhodamine, fluorescein, cyanine, and inorganic quantum dots.

In Example 20, the subject matter of Example 18 to 19 can optionally include the fluorescent conductive fill material including a fluorescent component comprising between about 0.5% and 50% by weight of the fluorescent conductive fill material.

Having thus described in detail embodiments of the present description, it is understood that the present description defined by the appended claims is not to be limited by particular details set forth in the above description, as many apparent variations thereof are possible without departing from the spirit or scope thereof.

What is claimed is:

1. A method of fabricating a microelectronic substrate, comprising:
    forming a substrate core having a first surface and an opposing second surface;
    forming a hole to extend from the substrate core first surface to the substrate core second surface defining at least one sidewall;
    forming a conductive material layer on the at least one substrate core hole sidewall;
    disposing a fluorescent conductive fill material to abut the conductive material layer and substantially fill the substrate core hole;
    illuminating an exposed portion of the fluorescent conductive fill material; and
    detecting anomalies in the light fluoresced by the exposed portion of the fluorescent conductive fill material.

2. The method of claim 1, wherein disposing the fluorescent conductive fill material comprises disposing a fluorescent conductive fill material comprising an epoxy resin having a fluorescent component dispersed therein.

3. The method of claim 1, wherein disposing the fluorescent conductive fill material comprises disposing a fluorescent conductive fill material including a fluorescent component selected from the group consisting of rhodamine, fluorescein, cyanine, and inorganic quantum dots.

4. The method of claim 1, wherein disposing the fluorescent conductive fill material includes disposing a fluorescent conductive fill material having a fluorescent component comprising between about 0.5% and 50% by weight of the fluorescent conductive fill material.

5. The method of claim 1, forming a conductive material layer on the at least one substrate core hole sidewall comprising depositing a conductive material layer on the substrate core first surface, the substrate core second surface, and the at least one substrate core hole sidewall.

6. The method of claim 5, wherein depositing the conductive material layer comprises depositing a substantially uniform layer of conductive material layer on the substrate core first surface, the substrate core second surface, and the at least one substrate core hole sidewall.

7. The method of claim 5, wherein depositing the conductive material layer comprises plating a metal material.

8. The method of claim 5, wherein plating a metal material comprises plating a metal material selected from the group consisting of copper, silver, gold, nickel, titanium, tungsten, and alloys thereof.

9. The method of claim 5, wherein disposing the fluorescent conductive fill material comprises disposing the fluorescent conductive fill material into the substrate core hole and over the conductive material layer proximate the substrate core first surface; and further including removing a portion of the fluorescent conductive fill material over the conductive material layer proximate the substrate core first surface.

10. The method of claim 5, wherein illuminating the exposed portion of the fluorescent conductive fill material comprises transmitting electromagnetic radiation toward the exposed portion of the fluorescent conductive fill material.

11. The method of claim 5, further including forming a first capping conductive material layer on the fluorescent conductive fill material and the conductive material layer proximate the substrate core first surface, forming a second capping conductive material layer on the fluorescent conductive fill material and the conductive material layer proximate the substrate core second surface, removing a portion of the first capping conductive material layer and the conductive material layer proximate on the substrate core first surface, and removing a portion of the second capping conductive material layer and the conductive material layer proximate to substrate core second surface to separate the conductive material layer into individual conductive material liners within each of substrate core holes and form first capping layers on the fluorescent conductive fill material proximate the substrate core first surface and second capping layers on the fluorescent conductive fill material proximate the substrate core second surface.

12. The method of claim 11, further including forming a top trace network proximate the substrate core first surface.

13. The method of claim 12, wherein the top trace network comprises a plurality of dielectric layers and a plurality of conductive traces formed on and extending through at least one of the plurality of dielectric layers.

14. The method of claim 11, further including forming a bottom trace network proximate the substrate core second surface.

15. The method of claim 14, wherein the bottom trace network comprises a plurality of dielectric layers and a plurality of conductive traces formed on and extending through at least one of the plurality of dielectric layers.

* * * * *